United States Patent
Zacche' et al.

(10) Patent No.: US 11,390,579 B2
(45) Date of Patent: Jul. 19, 2022

(54) PROCESS FOR THE PREPARATION OF ENANTIOMERICALLY PURE NOREPINEPHRINE

(71) Applicant: Edmond Pharma, s.r.l., Paderno Dugnano (IT)

(72) Inventors: Matteo Zacche', Nerviano (IT); Pier Andrea Gatti, San Genesio Ed Uniti (IT); Fulvio Gerli, Paderno Dugnano (IT); Davide Sbarbada, Cura Carpignano (IT); Fabio Rondina, Brugherio (IT)

(73) Assignee: Edmond Pharma, s.r.l., Paderno Dugnano (IT)

( * ) Notice: Subject to any disclaimer, the term of this patent is extended or adjusted under 35 U.S.C. 154(b) by 0 days.

(21) Appl. No.: 17/594,409

(22) PCT Filed: Apr. 2, 2020

(86) PCT No.: PCT/EP2020/059438
§ 371 (c)(1),
(2) Date: Oct. 15, 2021

(87) PCT Pub. No.: WO2020/212157
PCT Pub. Date: Oct. 22, 2020

(65) Prior Publication Data
US 2022/0089520 A1 Mar. 24, 2022

(30) Foreign Application Priority Data
Apr. 18, 2019 (EP) .................................. 19170053

(51) Int. Cl.
| C07C 213/08 | (2006.01) |
| C07C 223/02 | (2006.01) |
| C07C 221/00 | (2006.01) |
| B01J 31/22 | (2006.01) |
| B01J 23/44 | (2006.01) |
| B01J 31/18 | (2006.01) |

(52) U.S. Cl.
CPC ............. *C07C 213/08* (2013.01); *B01J 23/44* (2013.01); *B01J 31/1805* (2013.01); *B01J 31/2295* (2013.01); *C07C 221/00* (2013.01); *C07C 223/02* (2013.01); *B01J 2531/821* (2013.01); *C07B 2200/07* (2013.01); *C07C 2601/16* (2017.05)

(58) Field of Classification Search
None
See application file for complete search history.

(56) References Cited

PUBLICATIONS

STN abstract for Fodor et al. (Acta Chimica Academiae Scientiarum Hungaricae (1951), 1, 395-402) (Year: 1951).*
Fodor et al. (Acta Chim. Acad. Sci. Hung., 1951, vol. 1, 395). (Year: 1951).*
Egorov et al., A concise formation of N-substituted 3,4-diarylpyrroles-synthesis and cytotoxic activity, Org. Biomol. Chem. vol. 12, No. 9, Jan. 14, 2014, pp. 1518-1524.
Kershaw N M et al., "X-ray crystallography and computational docking for the detection and development of protein-ligand interactions", Current Medicinal Chemistry, vol. 20, No. 4, Jan. 1, 2013, pp. 569-575.
Reply to Search Opinion established by the EPO dated Apr. 1, 2020.
Search Report and Written Opinion of PCT/EP2020/059438 dated Jul. 6, 2020.

* cited by examiner

*Primary Examiner* — Sudhakar Katakam
*Assistant Examiner* — Jennifer C Sawyer
(74) *Attorney, Agent, or Firm* — Silvia Salvadori, P.C.; Silvia Salvadori

(57) ABSTRACT

The invention concerns a new, efficient process for the preparation of enantiomerically pure norepinephrine (also known as noradrenaline), or an addition salt thereof, using a catalytic hydrogenation system under hydrogen donor transfer. The invention also discloses a novel intermediate and the process for the preparation thereof.

16 Claims, No Drawings

PROCESS FOR THE PREPARATION OF ENANTIOMERICALLY PURE NOREPINEPHRINE

This application is a U.S. national stage of PCT/EP2020/059438 filed on 2 Apr. 2020, which claims priority to and the benefit of European Application No. 19170053.3 filed on 18 Apr. 2019, the contents of which are incorporated herein by reference in their entireties.

The invention concerns a new, efficient process for the preparation of enantiomerically pure norepinephrine (also known as noradrenaline), or an addition salt thereof, using a catalytic hydrogenation system under hydrogen donor transfer. The invention also discloses a novel intermediate and the process for the preparation thereof.

BACKGROUND OF THE INVENTION

Norepinephrine, which is also known as noradrenaline or arterenol, is a natural occurring compound which belongs to catecholamines class. In the human body, norepinephrine is a hormone and neurotransmitter whose main function is to mobilize the brain and body for action; pharmacologically it is used as a sympathomimetic. Being a sympathetic agent, norepinephrine stimulates adrenergic receptors causing vasoconstriction of different radial muscles and the sphincter of the gastrointestinal tract. Moreover, norepinephrine is the main neurotransmitter of the sympathetic nerves in the cardiovascular system and it is responsible for tonic and reflexive changes in cardiovascular tone.

Norepinephrine occurs naturally as levo-rotatory enantiomer, chemically 4-[(1R)-2-amino-1-hydroxyethyl]benzene-1,2-diol, and has the structure depicted in Formula I:

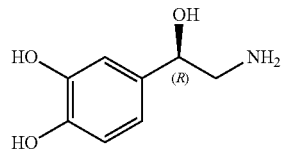

Formula I

Current industrial processes for manufacturing of (R)-norepinephrine comprise preparing 3,4-dihydroxy-α-amino-acetophenone (also named arterenone) by different reaction sequences and then reducing the latter by hydrogenation with metal catalysts to produce racemic norepinephrine, which is then resolved by formation of diastereoisomeric salt with L-(+)-tartaric acid.

U.S. Pat. No. 2,786,871 discloses that arterenone is obtained in 50% yield by reacting 3,4-dihydroxy-α-chloroacetophenone with ammonia. Arterenone may then be hydrogenated to obtain racemic norepinephrine. The process has the disadvantage of low yield and darkening of the reaction mixture which yields to a coloured product which is not suitable for pharmaceutical use.

WO 2013/008247 discloses the preparation of arterenone by reacting 3,4-dihydroxy-α-haloacetophenone with hexamine, followed by hydrolysis and hydrogenation to obtain racemic norepinephrine. This process has anyway the disadvantage to require the use of a chlorinated solvent, preferably chloroform, which is toxic and mutagenic, and its use is restricted for industrial use. Moreover, the hydrogenation yields a racemic material which has to be subjected to a further resolution step, drastically lowering the yields of the process and increasing the wastes.

Since the main problem in the formation of arterenone is the presence of a primary amino group in coexistence with a catechol moiety, arterenone itself may be alternatively substituted by a derivative in which either the catechol moieties are protected (for example acetylated) or in which the amino group is protected (for example benzylated). Anyway, there is very few literature for both these alternatives. In the case of protection of catechol moiety, the main drawback is that two steps must be added, protection and deprotection, which gives a longer and more tedious process and the risk of formation of impurities which are difficult to purify; protection/deprotection processes are scarcely used on an industrial scale process because of those reasons. In the case of protection of amino moiety, benzylamine could be used instead of ammonia to effect the condensation, and then the benzyl group would be eliminated by the same step of hydrogenation. Anyway, according to the literature, such compound is not stable. In fact, according to Egorov et al. (Org. Biomol. Chem., 2014, 12, 1518), the condensation of benzylamine with 2-chloro-3',4'-dihydroxyacetophenone leads to the unstable aminoketone depicted in Formula II:

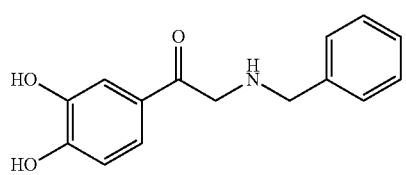

Formula II

As reported in the same reference, the compound is so unstable that it is not possible to isolate it but it is necessary to react it rapidly with another compound.

Another reference reports that attempts to prepare the monobenzylamino derivative of 2-chloro-3',4'-dihydroxyacetophenone were unsuccessful (Simonoff and Hartung, J. Am. Pharm. Assoc. 1946 Oct; 35(10):306-9). In yet another paper (Dakin, Proc. Roy. Soc., 76B,498(1905)) it is described that the failure of benzylamine and 3,4-dihydroxyphenacyl chloride to react as expected is due to the presence of the phenolic hydroxyl groups.

In general, all the known processes for the manufacturing of (R)-norepinephrine which rely on the hydrogenation of arterenone or a derivative thereof suffer from the main drawback that a racemic material is obtained, requiring further separation of enantiomers with loss of time and increased wastes.

For example, U.S. Pat. No. 2,774,789 discloses the resolution of dl-norepinephrine using tartaric acid, malic acid or N-benzoyl-L-threonine. Anyway, the yields of such process are fairly low, as from 169 g of racemate it is obtained 60-85 g of tartrate salt monohydrate, which corresponds to about 30-40 g of (R)-norepinephrine. This quantity corresponds to a yield of 47% on the theoretical molar amount, which in turn means a yield of 23% with respect to the starting quantity of racemate, i.e. wasting 77% of the product mass. The mother liquors may then be recovered and racemized to obtain some material to be resolved again, but this is a tedious and time-consuming task. This process is obviously very inefficient in view of yields, waste generation and required time.

An enantioselective process is reported in CN 108069863, which describes the reduction of arterenone with a chiral borane reagent such as (−)-diisopropyldiisopinocampheyl chloroborane. The reported examples show that to obtain an enantiomerical purity of at least 99.0%, which would be suitable for pharmaceutical use, the reaction must be conducted at very low temperatures such as −30° C. Maintaining such low temperature in the plant is not a trivial task, and the cost of the equipment suitable for conducting reactions at such a low temperature limits the industrial applicability of the process.

Moreover, a large excess of the reducing reagent is necessary, described as 2.5 to 3.0 moles equivalent. In fact, as reported in the example of the patent, for 16.7 g of arterenone a quantity as high as 150 g of borane reagent must be used, which is almost ten times in terms of mass. The reagent is then consumed and discarded as waste, and cannot be recovered by any means. The borane reagent is not directly available on the market and it is rather expensive to manufacture; it has to be manufactured in-house with a tedious procedure, which uses safety concerning reagents, must be stored at controlled temperature under inert gas and must be used in a short period of time because it is an unstable reagent.

Given all of these considerations, this manufacturing process is obviously not suitable for industrial manufacturing, due to its many disadvantages. Kershaw N M et al. "X-ray crystallography and computational docking for the detection and development of protein-ligand interactions.", Curr Med Chem. 2013; 20(4):569-75, disclose the preparation of compounds by subjecting compounds of formula IV to protection, reduction and reaction with benzylamine.

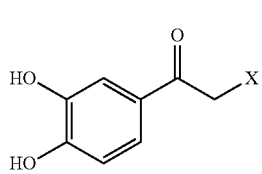

IV

Surprisingly, no other enantioselective processes are known for the manufacture of a single enantiomer of norepinephrine. This is particularly surprising, because the molecule was discovered in the early 20$^{th}$ Century and for more than a century it has played a central role in pharmacology and patient care. Even more surprisingly, for almost all the other molecules of the catecholamine class, such as adrenaline or phenylephrine, which have the same biological and pharmacological role, one or more enantioselective manufacturing methods have been reported in the literature.

There is thus a need for an efficient process for the preparation of pharmacologically useful (R)-norepinephrine, which is suitable for the industrial preparation and suitable for the use as a pharmaceutical ingredient. The main goal of such a new process, given the drawbacks mentioned above, is the need of an enantioselective process (i.e. yielding a single enantiomer with at least 99.0% chiral purity or more), which uses catalytic reagents and generates low amount of wastes, using conditions suitable for a common chemical plant and following a procedure which is simple, timely and cost-effective. Also, the new process aims at using an intermediate which is easily prepared and with enough stability for industrial manufacturing, which does not require toxic or mutagenic reagents, and is obtained with a quality profile suitable for pharmaceutical manufacturing.

DESCRIPTION OF THE INVENTION

The present invention provides a new, efficient enantioselective process for the preparation of a single enantiomer of norepinephrine by catalytic asymmetric hydrogenation effected on a novel intermediate, and which overcomes all the above mentioned drawbacks of the prior art. Particularly useful under the conditions of the novel process is the preparation of (R)-norepinephrine, which is the pharmacological interesting enantiomer.

The present invention provides a process for the preparation of a single enantiomer of norepinephrine, or of an addition salt thereof, the process comprising the following steps:

a) reacting a compound of formula (IV)

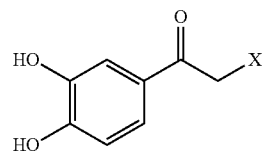

Formula IV wherein X is halogen (F, Cl, Br, I), with benzylamine is a suitable solvent, using an auxiliary base, under the atmosphere of an inert gas, and isolating the resulting condensation product as an acid addition salt with a carboxylic acid, to give a compound of formula (III)

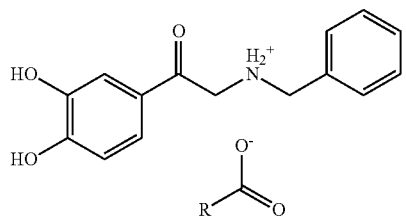

Formula III wherein R is hydrogen, or the residue of an aliphatic, cycloaliphatic or aromatic monocarboxylic or dicarboxylic acid;

b) enantioselective reduction of the benzylamino ketone acid addition salt of Formula III to give a single enantiomer of the benzylamino alcohol of Formula V

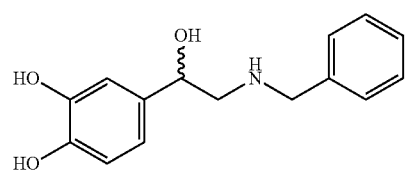

Formula V wherein the carbon atom bearing the waxy bond can be in the (R) or (S) configuration;

c) debenzylation of the single enantiomer of the compound of Formula V to give a single enantiomer of norepinephrine;

d) isolating the single enantiomer of norepinephrine as a free base or acid addition salt thereof.

Further objects of the invention are the novel intermediates of Formula III.

DETAILED DESCRIPTION OF THE INVENTION

In one embodiment, the present invention provides a novel intermediate for the preparation of a single enantiomer of norepinephrine. In one embodiment the single enantiomer of norepinephrine is (R)-norepinephrine of Formula (I).

Surprisingly, it has been found that the unstable benzylamino ketone of Formula II described above, may be prepared in a reproducible and industrially convenient way, when the obtained condensation product is isolated as an acid addition salt with a carboxylic acid of the above depicted general Formula III.

In the general formula III, the carboxylic acid may be any aliphatic, including cycloaliphatic, mono- or di-carboxylic acid and aromatic mono- and di-carboxylic acid. As used herein in the above general Formula III, R is hydrogen, a carboxyl group, an alkyl radical, preferably of 1 to 17 carbon atoms, or an aryl radical, preferably of not more than 12 carbon atoms, said alkyl, cycloalkyl and aryl radical being optionally substituted by a further carboxyl group Examples of carboxylic acids are formic, acetic, propionic, oxalic, malonic, succinic, benzoic, toluic, o-phthalic, tartaric, and the like.

Accordingly, the present invention provides a process for the preparation of the compound of Formula III by reacting a compound of Formula IV

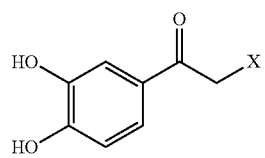

Formula IV wherein X is halogen (F, Cl, Br, I), with benzylamine is a suitable solvent, using an auxiliary base, under the atmosphere of an inert gas, for example nitrogen, and isolating the resulting condensation product as an acid addition salt with a carboxylic acid.

In a preferred embodiment, the compound of Formula IV is 2-chloro-3',4'-dihydroxy acetophenone, i.e. X=Cl. In fact, among all the compounds of general Formula IV, this is the most stable one and the most suitable for industrial use.

The reaction is performed under an atmosphere of an inert gas, typically nitrogen, to avoid contact between oxygen and the reaction mixture. In fact, when oxygen is present, radical oxidative reactions may occur, lowering both product purity and yield for the process.

The auxiliary base used for the reaction is selected to have a pK equal to or higher than 10, as it should extract the proton from at least one of the catechol moieties; such base may be organic or inorganic. Examples of suitable inorganic bases include metal hydrides or metal hydroxides or alkoxides such as sodium hydroxide, sodium hydride, sodium methoxide, potassium tert-butoxide and sodium tert-butoxide. Examples of suitable organic bases include amines such as triethylamine, 1,8-diazabicyclo[5.4.0]undec-7-ene or 1,4-diazabicyclo[2.2.2]octane, or benzylamine. The use of triethylamine, which is commonly available, safe and inexpensive is particularly advantageous from an industrial point of view.

The auxiliary base is used in 1 to 10 mole equivalents with respect to 2-chloro-3',4'-dihydroxyacetophenone, preferably in 1 to 5 mole equivalents and most preferably in 1 to 2 mole equivalents.

Benzylamine may be used in a molar ratio of 1:1 to 1:10 to 2-chloro-3',4'-dihydroxyacetophenone. Particularly useful from an industrial point of view is the use of benzylamine in molar excess with a factor of 1.5:1 to 5:1 to 2-chloro-3',4'-dihydroxyacetophenone. Preferably, the excess ratio should be 3:1 to 5:1, most preferably 4:1 molar excess, which gives the best ratio between yields and industrial costs.

Suitable solvents are organic solvents which are stable under basic conditions, or water. Suitable organic solvents include ethers, cyclic ethers, hydrocarbons, halocarbons, sulfoxides or mixtures thereof. Examples of such solvents are, but are not limited to, diethyl ether, tetrahydrofuran, 1,4-dioxane, toluene, xylene, methylene chloride or dimethylsulfoxide. In a preferred embodiment, water is used as a solvent, as it is a safe solvent when compared to any organic solvent, and provides a reaction mixture in a complete solution, which gives a stable homogeneous reaction system and faster reaction times when compared to heterogeneous reaction systems.

The temperature of the reaction is kept between 10° C. and the reflux temperature of the solvent, preferably between 20° C. and 60° C. In a preferred embodiment, where the solvent is water, a temperature between 35° C. and 50° C., provides the best results in terms of yield, purity and reaction times. Higher temperatures would result in lower times but higher impurity profile and lower yield, while lower temperatures would result in prolonged reaction times.

After completion of the reaction, the mixture is quenched with a mono- or dicarboxylic acid of general formula R—COOH where R is as defined above. In a preferred embodiment, the carboxylic acid is formic (R=H, Compound A) or acetic (R=CH$_3$, Compound B) acid.

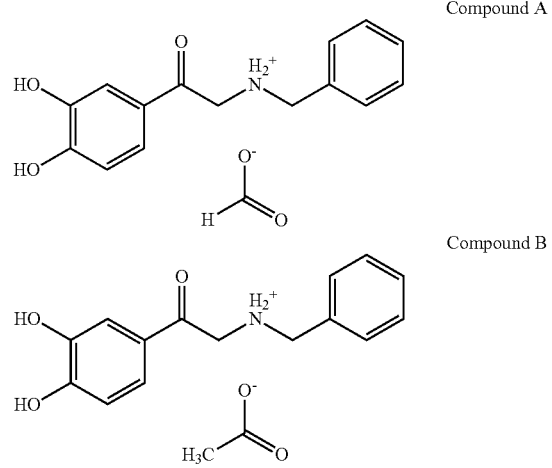

The carboxylic acid is conveniently used in an equivalent or slight excess amount relative to the total moles of bases used during the condensation, i.e. to cover both the moles of auxiliary base and the moles of benzylamine which are used in the reaction. The pH at the end of the carboxylic acid addition should be in the range of a diluted solution of such carboxylic acid in water, hence for example when acetic acid is used the pH should be around 4. This ensures the neutralization and stabilization of the condensation product. Once the pH is in the correct range, the acid addition salt of the product directly precipitates from the solvent, or when using water, a water-soluble solvent is added to precipitate the acid addition salt from the solution. Such water-soluble solvent is selected amongst the solvents in which the compound of Formula III is not soluble; suitable solvents are alcohols, cyclic ethers or ketones; the choice of solvent is directly related to the carboxylic acid chosen to quench the reaction, as the acid addition salt has different solubility properties based on the acidic moiety itself. Examples of such solvents are, but are not limited to, methanol, isopropanol, ethanol, tetrahydrofuran, 1,4-dioxane, acetone, methyl-ethyl ketone, and so on. In a preferred embodiment, when water is used as solvent and acetic or formic acid for quenching, the preferred water-soluble solvent is acetone, as it is readily available, inexpensive and gives the best results in terms of yield and purity.

The obtained product is then isolated by filtration or other similar methods. The resulting product may be further purified, e.g. by crystallization or trituration with a solvent, or it may submitted to the next step of the process to prepare a single enantiomer of norepinephrine.

In fact, in a second aspect of the invention, it has surprisingly been found that a benzylamino ketone acid addition salt of Formula III can be enantioselectively reduced to the novel benzylamino alcohol of Formula V.

The novel intermediate of Formula V may be de-benzylated to obtain a single enantiomer of norepinephrine.

In a preferred embodiment the single enantiomer of norepinephrine is (R)-norepinephrine and the sequence of steps b) and c) of the process of the invention to prepare (R)-norepinephrine is depicted in Scheme 1 wherein R is as defined above:

SCHEME 1

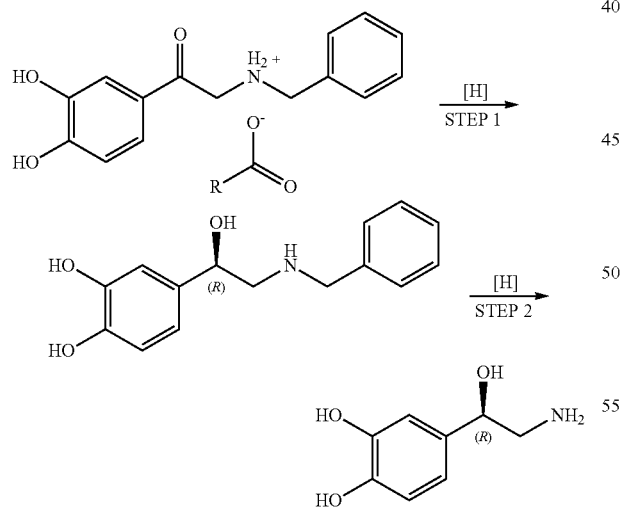

The process is conveniently run one-pot with the two reductions of steps b) and c) performed sequentially without isolating intermediate products, which is a method most suitable for industrial preparation. It would nonetheless be possible to isolate the intermediate of Formula V or an acid addition salt thereof if needed, without limiting the scope of the invention.

The reaction according to the scheme above comprises the following steps:

STEP 1: Reacting a compound of Formula III with hydrogen or an hydrogen source in the presence of a suitable catalyst, in an alcoholic or hydroalcoholic solvent, to obtain enantioselectively a compound of Formula V.

Optionally isolating the compound of Formula V as a free base or acid addition salt thereof.

STEP 2: Reacting compound of Formula V with hydrogen or a hydrogen source, in the presence of a suitable catalyst, in an alcoholic or hydroalcoholic solvent, to obtain a single enantiomer of norepinephrine.

Isolating the single enantiomer of norepinephrine as a free base or acid addition salt thereof.

As stated above, the most useful system for an industrial preparation is a one-pot reaction, in which Step 1 is completed with one catalyst and the obtained compound of Formula V is reacted in-situ with the second catalyst to remove the protecting benzyl group. In this process, steps 1 and 2 both use the same solvent mixture and the same hydrogen source.

The solvent used for the reaction is a C1 to C3 alcohol, methanol, ethanol, propanol or isopropanol are preferred, most preferably methanol. The solvent may optionally contain water. In a preferred embodiment, a 9:1 mixture methanol/water is used as reaction medium.

Sources of hydrogen may be molecular hydrogen or a hydrogen donor under transfer hydrogenation system. Transfer hydrogenations are well known methods; suitable examples of hydrogen donors include isopropanol with potassium hydroxide, formic acid/triethylamine buffers, sodium formate buffers, formic acid, or mixtures thereof. In a preferred embodiment, formic acid is used, which decomposes into hydrogen and carbon dioxide under heating.

Suitable catalysts for the enantioselective reduction in Step 1 are ruthenium (II) complexes with a sulfonamide derivatized diphenyl ethylenediamine of "tethered" type. Such class of catalysts have been disclosed by M. Wills et al in J. Am. Chem. Soc. 2005, 127, 7318 and by R. Hodgkinson et al in Organometallics, 2014, 33(19), 5517-5524 and are depicted by the general Formula VI Formula VI

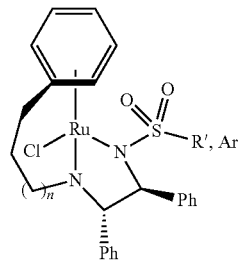

In the above formula, n is the integer 1 or 2 and the sulfonamide moiety can be an alkyl- or aryl-sulfonamide, corresponding, respectively, to the radical R' or Ar. The "tether" lateral chain is an alkylene chain of 3 (n=1) or 4 (n=2) carbon atoms. The two stereocenters bearing the phenyl groups of the ethylenediamine moiety may be (R, R) or (S, S). When using the (R, R) enantiomer, one of the enantiomers of norepinephrine is obtained, while when using the (S, S) enantiomer, the other one is obtained. In particular, when using the (S, S) enantiomer, the pharmacologically active (R)-norepinephrine is obtained.

Examples of commercially available catalysts of Formula VI with a tether (teth) of three or four carbon atoms include C3-[(S,S)-teth-TsDPEN-RuCl], [(S,S)-teth-MtsDPEN-RuCl], C3-[(S,S)-teth-MesDPEN-RuCl], C3-[(S,S)-teth-TrisDPEN-RuCl], C4-[(R,R)-teth-TrisDPEN-RuCl], C4-[(S,S)-teth-TsDPEN-RuCl] and C4-[(S,S)-teth-MsDPEN-RuCl]. In these formulae, the R' or Ar group is tosyl (Ts), mesytilyl (Mts), mesyl (Mes) or triisoproylphenyl (Tris), and the prefix C3 or C4 indicates the presence of a tether (teth) with three or four carbon atoms, respectively.

Preferably the catalyst used for the preparation of (R)-norepinephrine is selected from the group of C3-[(S,S)-teth-TsDPEN-RuCl], C3-[(S,S)-teth-MtsDPEN-RuCl], C3-[(S,S)-teth-MesDPEN-RuCl], and C3-[(S,S)-teth-TrisDPEN-RuCl]. More preferably, the catalyst is C3-[(S, S)-teth-TsDPEN-RuCl], which gives the best results in terms of enantiomeric purity, reaction times and catalyst load.

(R)-Norepinephrine is thus obtained in high enantiomeric purity of 99% or more, as assayed by HPLC analysis.

The catalyst used in Step 2 is selected from common catalyst used in deprotection of the benzyl group. Preferably, the catalyst is palladium, more preferably palladium on charcoal.

The obtained single enantiomer of norepinephrine is then recovered either as a free base or as acid addition salt thereof. Particularly useful from an industrial point of view, is the isolation of (R)-norepinephrine as tartrate salt, to obtain the pharmaceutically useful active ingredient (R)-norepinephrine bitartrate monohydrate. Nonetheless, it is possible to isolate it as a different acid addition salt, for example for further purification if needed, and to convert such salt in a second step to the bitartrate salt, without limiting the scope of the invention itself. The obtained product is then isolated by filtration or other similar methods.

In a preferred embodiment, (R)-norepinephrine is recovered as oxalate if further purification is needed, or as tartrate to directly obtain the marketed active pharmaceutical ingredient.

In a preferred embodiment, thus, (R)-norepinephrine is prepared as oxalic or tartaric acid addition salt by a process which comprises:

Reacting 2-chloro-3',4'-dihydroxy acetophenone with benzylamine in water using triethylamine as auxiliary base.

Quenching the reaction with formic or acetic acid and precipitating a compound of Formula III by addition of acetone.

Reacting a compound of Formula III in a mixture of methanol and water with formic acid as hydrogen source, using C3-[(S, S)-teth-TsDPEN-RuCl] as catalyst for the enantioselective reduction.

Adding Palladium on charcoal to the reaction mixture to remove the benzyl protecting group.

Precipitating (R)-norepinephrine as oxalic or tartaric acid addition salt.

Therefore, the present invention discloses a simple, economical, efficient, robust, ecologically friendly and suitable process for the preparation of a single isomer of norepinephrine, in particular of (R)-norepinephrine, in high yields and high purity with an enantiomeric purity higher than 99%.

The following examples further illustrate the invention.

EXAMPLE 1

Preparation of 2-benzylamino-3',4'-dihydroxyacetophenone acetate (Compound B)

Water (1.3 kg) and 2-chloro-3',4'-dihydroxyacetophenone (1 kg) are charged in an inertized reactor. Triethylamine (0.67 kg) is added to the resulting suspension without exceeding 30° C. to obtain a solution. Benzylamine (2.4 kg) is added dropwise without exceeding 50° C. At the end of addition, the mass is kept under stirring at 50° C. for about 2 hours, then cooled to about 10° C. and added with a mixture of acetone (1.6 kg) and acetic acid (1.8 kg) under nitrogen without exceeding 25° C. The reaction mixture is cooled to about 10° C. then acetone (2 kg) is added and the product is filtered to obtain (after drying) 1 kg of 2-benzylamino-3',4'-dihydroxyacetophenone acetate.

EXAMPLE 2

Preparation of 2-benzylamino-3',4'-dihydroxyacetophenone acetate (Compound B)

Water (30 g) and 2-chloro-3',4'-dihydroxyacetophenone (10 g) are charged in a reactor under nitrogen. Benzylamine (31 g) is added dropwise without exceeding 35° C. At the end of addition, the mass is kept under stirring at 45° C. for about 2 hours, then cooled to about 10° C. and added with a mixture of acetone (8 g) and acetic acid (18 g) under nitrogen without exceeding 25° C. The reaction mixture is cooled to about 10° C., then acetone (72 g) is added and the product is filtered, then suspended in acetone (27 g) and stirred at room temperature for about 30 minutes, then filtered to obtain (after drying) 8 g of 2-benzylamino-3',4'-dihydroxyacetophenone acetate.

EXAMPLE 3

Preparation of 2-benzylamino-3',4'-dihydroxyacetophenone formate (Compound A)

Water (45 g) and 2-chloro-3',4'-dihydroxyacetophenone (30 g) are charged in a reactor under nitrogen. Triethylamine (20 g) is added to the resulting suspension add without exceeding 30° C. Benzylamine (72 g) is added dropwise without exceeding 45° C. At the end of addition, the mass is kept under stirring at 45-50° C. for about 2 hours, cooled to about 10° C. and a mixture of acetone (24 g) and formic acid (54 g) is added under nitrogen without exceeding 25° C. The reaction mixture is cooled to about 10° C., acetone (48 g) is added, then the product is filtered to obtain (after drying) 39 g of 2-benzylamino-3',4'-dihydroxyacetophenone acetate.

EXAMPLE 4

Preparation of 2-benzylamino-1-(3',4'-dihydroxyphenyl)-ethanol (Compound of Formula V)

Isopropanol (90 mL), water (10 mL), formic acid (3 mL), Compound B (20 g) and C3-[(S,S)-teth-MesDPEN-RuCl] (30 mg) are charged in the flask. The mixture is heated to reflux for 30 minutes and then formic acid (6 mL) is added dropwise. The mixture is heated to reflux for 2 hours, diluted with isopropanol (100 mL) and neutralized with ammonia to pH 8. The solid is filtered, washed with isopropanol and dried under vacuum to obtain 15 g of 2-benzylamino-1-(3',4'-dihydroxyphenyl)-ethanol.

EXAMPLE 5

Preparation of 2-benzylamino-1-(3',4'-dihydroxyphenyl)-ethanol (Compound of Formula V)

Methanol (180 mL), water (20 mL), formic acid (6 mL), Compound B (40 g) and C3-[(S,S)-teth-MtsDPEN-RuCl] (50 mg) are charged in the flask. The mixture is heated to reflux for 30 minutes and then formic acid (12 mL) is added dropwise. The mixture is heated to reflux for 2 hours, concentrated to dryness, diluted with water (200 mL) and isopropyl ether (200 mL). The biphasic mixture is neutralized with triethylamine to pH 8. The solid is filtered, triturated with isopropanol, filtered again and finally dried under vacuum to obtain 28 g of 2-benzylamino-1-(3',4'-dihydroxyphenyl)-ethanol.

EXAMPLE 6

Preparation of (R)-norepinephrine bitartrate

Compound B (300 g), methanol (1.8 L), water (1.2 L), C3-[(S,S)-teth-TsDPEN-RuCl] (0.6 g) and formic acid (50 mL) are charged in the reactor. The mixture is heated to reflux and formic acid (38 mL) is added dropwise. The solution is heated to reflux for 2 hours then Pd/C 10% (30 g) is added. The mixture is heated to reflux and formic acid (88 mL) is added dropwise. After 3 hours of reflux, the mixture is filtered to remove the catalyst and L-(+)-tartaric acid (261 g) is added. The solution is concentrated under vacuum and the residue is dissolved in ethanol (600 mL) and purified water (200 mL). The solution is seeded and cooled, then filtered and washed to obtain 168 g of norepinephrine bitartrate monohydrate.

EXAMPLE 7

Preparation of (R)-norepinephrine bitartrate

Compound B (100 g), ethanol (450 mL), water (50 mL), C3-[(S,S)-teth-TsDPEN-RuCl] (0.15 g) and formic acid (15 mL) are charged in the reactor. The mixture is heated to 60° C. for 1 hour and formic acid (15 mL) is added dropwise. The solution is heated to reflux for 2 hours then activated carbon (10 g) is added. The mixture is filtered and charged back in the reactor, then Pd/C 10% (11 g) is added. The mixture is heated to reflux and formic acid (15 mL) is added dropwise. After 3 hours of reflux, the mixture is filtered to remove the catalyst and L-(+)-tartaric acid (87 g) is added. The solution is seeded and cooled, then filtered and washed to obtain 93 g of norepinephrine bitartrate monohydrate.

EXAMPLE 8

Preparation of (R)-norepinephrine oxalate

Compound A (35 g), methanol (160 mL), water (18 mL), C3-[(S,S)-teth-TsDPEN-RuCl] (0.07 g) and formic acid (5 mL) are charged in the reactor. The mixture is heated to about 50° C. for 1 hour and formic acid (5 mL) is added dropwise. The solution is heated to reflux for 3 hours then activated carbon (3 g) is added. The mixture is filtered and charged back in the reactor, then Pd/C 10% (3.5 g) is added. The mixture is heated to reflux and formic acid (5 mL) is added dropwise. After 3 hours at about 50° C., formic acid (5 mL) is added dropwise. After 2 more hours at about 50° C., the mixture is filtered to remove the catalyst and oxalic acid (8.6 g) is added. The solution is seeded and cooled, then filtered and washed to obtain 11 g of norepinephrine oxalate are obtained.

EXAMPLE 9

Preparation of (R)-norepinephrine oxalate

Methanol (9 L), water (1 L), formic acid (290 mL) and C3-[(S,S)-teth-TsDPEN-RuCl] (4 g) are charged in the reactor. Compound B (2 kg) is added to the solution. The mixture is heated at about 60° C. for 2 hours, then formic acid (290 mL) is added dropwise and the mixture is heated at about 60° C. for 3 hours. Formic acid (290 mL) is added dropwise and the mixture is heated additionally at about 60° C. for 2 hours, then the solution is filtered on activated carbon cartridge and charged back in the reactor. Pd/C 10% (200 g) and formic acid (290 mL) are added to the solution and heating at about 60° C. is continued for 2 hours, then formic acid (290 mL) is added dropwise and heating is continued for additional 2 hours. The mixture is filtered and oxalic acid dihydrate (490 g) is added to the filtered solution. The crystallized mixture is cooled, filtered and dried to obtain 1 kg of norepinephrine oxalate.

EXAMPLE 10

Preparation of (R)-norepinephrine bitartrate monohydrate

Norepinephrine oxalate (0.7 kg), sodium metabisulfite (5 g), EDTA (5 g) and water (4.6 L) are charged in the reactor. At about 60° C., potassium carbonate (0.6 kg) is added, then the mixture is cooled and filtered and dried to obtain 530 g of norepinephrine base. This solid is suspended in water (500 mL) and ethanol (900 mL), and L-(+)-tartaric acid (470 g) is added; the mixture is heated at 50° C. to obtain a solution, which is filtered to remove foreign matter then cooled to obtain crystallization. The solid is filtered, washed and dried to obtain 890 g of norepinephrine bitartrate monohydrate.

The invention claimed is:
1. A process for the preparation of a single enantiomer of norepinephrine or of an addition salt thereof, the process comprising the following steps:
a) reacting a compound of formula (IV)

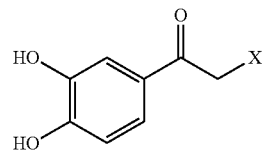

Formula IV wherein X is halogen (F, Cl, Br, I), with benzylamine in a suitable solvent, using an auxiliary base, under the atmosphere of an inert gas, and isolating the resulting condensation product as an acid addition salt with a carboxylic acid, to give a compound of formula (III)

Formula III

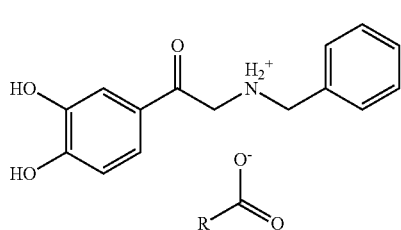

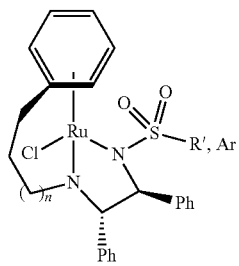

VI wherein R is hydrogen, or the residue of an aliphatic, cycloaliphatic or aromatic monocarboxylic or dicarboxylic acid;

b) enantioselective reduction of the benzylamino ketone acid addition salt of Formula III to give a single enantiomer of the benzylamino alcohol of Formula V Formula V

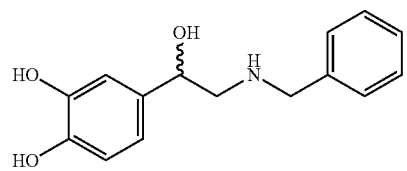

wherein the carbon atom bearing the waxy bond can be in the (R) or (S) configuration;

c) debenzylation of the single enantiomer of the compound of Formula V to give a single enantiomer of norepinephrine, and d) isolating the single enantiomer of norepinephrine as a free base or acid addition salt thereof.

2. The process of claim 1 wherein in the compound of formula III R is selected from the group of hydrogen, a carboxyl group, an alkyl radical having from of 1 to 17 carbon atoms, or an aryl radical of not more than 12 carbon atoms, said alkyl, cycloalkyl and aryl radical being optionally substituted by a further carboxyl group.

3. The process of claim 1 wherein in step a) in the compound of formula IV X is Cl, the solvent is water and the auxiliary base is triethylamine or benzylamine.

4. The process of claim 1 wherein in step a) the carboxylic acid is selected from the group consisting of formic, acetic, propionic, oxalic, malonic, succinic, benzoic, toluic, o-phthalic and tartaric acid.

5. The process of claim 1, wherein step b) comprises reacting a compound of Formula III with hydrogen or an hydrogen source in the presence of a suitable catalyst, to obtain enantioselectively a compound of Formula V and optionally isolating the compound of Formula V as a free base or acid addition salt thereof.

6. The process of claim 5, wherein said suitable catalyst is selected from the group of compounds defined by Formula VI wherein:

n is the integer 1 or 2; and

R' and Ar are selected form the group of tosyl (Ts), mesytilyl (Mts), mesyl (Mes) and triisoproylphenyl (Tris) and the two stereocenters bearing the phenyl groups of the ethylenediamine moiety are (R, R) or (S, S), to obtain enantioselectively a compound of Formula V as defined in claim 1.

7. The process of claim 6, wherein in the compounds of formula VI n is 1 and the catalyst is selected from the group of C3-[(S,S)-teth-TsDPEN-RuCl], C3-[(S,S)-teth-MtsDPEN-RuCl], C3-[(S,S)-teth-MesDPEN-RuCl], and C3-[(S,S)-teth-TrisDPEN-RuCl].

8. The process of claim 1, wherein step c) comprises reacting compound of Formula V with hydrogen or a hydrogen source, in the presence of a suitable catalyst.

9. The process of claim 8 wherein said suitable catalyst is palladium.

10. The process of claim 1, wherein steps b) and c) are performed in a $C_1$-to $C_3$ alcohol optionally containing water.

11. The process of claim 1, wherein steps b) and c) are performed in one-pot modality.

12. The process of claim 1, which comprises isolating the compound of Formula V as a free base or as an acid addition salt thereof.

13. The process of claim 1 wherein the single enantiomer of norepinephrine is (R)-norepinephrine.

14. The process of claim 1 for the preparation of (R)-norepinephrine as oxalic or tartaric acid addition salt, said process comprising the following steps:

i) Reacting 2-chloro-3',4'-dihydroxy acetophenone with benzylamine in water using triethylamine as auxiliary base;

ii) Quenching the reaction with formic or acetic acid and precipitating a compound of Formula III wherein R is H or methyl by addition of acetone;

iii) Reacting said compound of Formula III in a mixture of methanol and water with formic acid as hydrogen source, using C3-[(S, S)-teth-TsDPEN-RuCl] as catalyst for the enantioselective reduction;

iv) Adding Palladium on charcoal to the reaction mixture to remove the benzyl protecting group; and v) Precipitating (R)-norepinephrine as oxalic or tartaric acid addition salt.

15. The process of claim 4 wherein in step a) the carboxylic acid is selected from formic acid and acetic acid.

16. The process of claim 7, wherein in the compounds of formula VI n is 1 and the catalyst is C3-[(S, S)-teth-TsDPEN-RuCl].

* * * * *